United States Patent [19]

Tkachuk et al.

[11] Patent Number: 5,571,799

[45] Date of Patent: Nov. 5, 1996

[54] (2'-5') OLIGOADENYLATE ANALOGUES USEFUL AS INHIBITORS OF HOST-VS.-GRAFT RESPONSE

[75] Inventors: Zenovy Tkachuk; Eugeny Kvasyuk; Gennady Matsuka; Igor Mikhailopulo, all of Kiev, U.S.S.R.

[73] Assignee: Basco, Ltd., Washington, D.C.

[21] Appl. No.: 185,795

[22] PCT Filed: Aug. 12, 1991

[86] PCT No.: PCT/US91/05734

§ 371 Date: Aug. 29, 1994

§ 102(e) Date: Aug. 29, 1994

[87] PCT Pub. No.: WO93/03733

PCT Pub. Date: Mar. 4, 1993

[51] Int. Cl.⁶ .................... A61K 31/70; C07H 19/167
[52] U.S. Cl. ........................................ 514/47; 536/25.5
[58] Field of Search ........................ 514/44; 536/25.5

[56] References Cited

U.S. PATENT DOCUMENTS

| | | | |
|---|---|---|---|
| 4,378,352 | 3/1983 | Kimchi et al. | 424/180 |
| 4,464,359 | 8/1984 | Suhadolnik et al. | 424/180 |
| 4,515,781 | 5/1985 | Torrence et al. | 514/46 |
| 4,539,313 | 9/1985 | Suhadolnik et al. | 514/47 |
| 4,708,935 | 11/1987 | Suhadolnik et al. | 435/91 |
| 4,859,768 | 8/1989 | Suhadolnik et al. | 536/27 |
| 4,924,624 | 5/1990 | Suhadolnik et al. | 47/58 |
| 4,990,498 | 2/1991 | Suhadolnik | 514/47 |

*Primary Examiner*—Gary L. Kunz
*Attorney, Agent, or Firm*—Armstrong, Westerman, Hattori, McLeland & Naughton

[57] ABSTRACT

The invention deals with the production of analogues of adenylyl (2'-5')adenylyl (2'-5')-9-(2,3-anhydro-β-D-ribofuranosyl) adenine disodium salt by the phosphotriester method. The pharmaceutical composition prepared according to this invention inhibits the host-vs.-graft response.

8 Claims, 2 Drawing Sheets

*THE SYNTHESIS SCHEME OF ADENYLYL (2'-5')ADENYLYL (2'-5')-9-(2,3-ANHYDRO-B-D-EPOXYFURANOSYL ADENINE (DISODIUM SALT)

THE SYNTHESIS SCHEME OF ADENYLYL (2'-5') ADENYLYL
(2'-5')-9-(2,3-ANHYDRO-β-D-LYXOFURANOSYL ADENINE
(DISODIUM SALT)

5,571,799

(2'-5") OLIGOADENYLATE ANALOGUES USEFUL AS INHIBITORS OF HOST-VS.-GRAFT RESPONSE

FIELD OF THE INVENTION

Novel (2'-5')oligoadenylate analogues have been synthesized by the phosphotriester method, specifically adenylyl (2'-5')adenylyl (2'-5')-9-( 2,3-anhydro-β-D-lyxofuranosyl)adenine disodium salts [(2'-5')$A_2A^{l-epoxy}$], and adenylyl (2'-5')adenylyl (2'-5')-9-(2,3-anhydro-β-D-ribofuranosyl)adenine disodium salts [(2'-5')$A_2A_{r-epoxy}$]. Their action is directed to the modulation of both the helper and killer T-lymphocyte cells of the immune system. Unlike the commonly used cyclosporine, inhibitory action of (2'-5')oligoadenylate analogues does not suppress the anti-bacterial and anti-viral defense mechanism of the host. This compensatory effect on the immune system is accompanied by the appearance of increased amounts of α-interferon and γ-interferon in the lymphocytes, an elevated level of phagocytosis along with a decrease of α-interferon in blood plasma and a decrease of interleukin-II in lymphocytes. The invention is useful in appropriate concentrations to suppress the division of T-helper and T-killer cells and is useful to treat diseases connected with the disturbance of T-cellular immunity, e.g., autoimmune diseases, viral diseases, lymphocytic tumor and organ transplant rejection.

STATE OF THE PRIOR ART

In connection with the dissemination and recognition of autoimmune diseases and the introduction of organ and tissue transplantation a dire need arose for novel, non-toxic, immunosuppressive drugs.

Presently, various cyclopeptides, steroids and antimetabolites are used as immunosuppressants, primary among them being cyclosporine.

The goal when using any immunosuppressive drug in organ and tissue transplantation is to achieve an effective prevention of the acute and chronic transplant rejection (host-vs.-graft rejection), while keeping infections and other side effects to a minimum. The latter result from the high toxicity of the three types of immunosuppressors mentioned above.

The (2'-5')oligoadenylate [(2'-5']$A_3$], proposed by Kimchi et al., 1983, U.S. Pat. No. 4,378,352, as an immunesuppressor, inhibits the in vitro blast-transformation of T-lymphocytes, but when applied in vivo, it did not suppress the number of T-helper and T-killer cells, the principal targets of the post-transplantation immunosuppressors.

The rapid hydrolysis of 2'-5'$A_3$ by phosphodiesterase may explain the absence of its in vivo immunosuppressive action.

Analogues of (2'-5')oligoadenylate modified in 2' and 3' positions of the ribose fragment, which are key positions for the recognition necessary for the phosphodiesterase splitting, do not break down in vivo and thus are capable of manifesting their immunosuppressive property to the fullest.

In vitro administration of analogues of (2'-5')oligoadenylates have been shown to suppress the biosynthesis of DNA, RNA, and proteins (Kerr et al., G. B. No. 2,002,773, 3/1979, Johnston, Torrence, 1984)[1], show antiviral activity (Suhadolnik et al., U.S. Pat. No. 4,464,359, 8/1984, Montefiori, Sobol, Wu et al , 1989)[2], affect the natural killer activity (Black, Henderson, Pfleiderer et al., 1984), act as antimitogens (Eppstein, Schryver, Marsh, et al., 1983)[3] and as mediators of the action of interferon (Imbach J. et al., U.S. Pat. No. 4,476,301 10/1984).

[1]Johnston M. I., Torrence P. F., The role of interferon-induced proteins, double-stranded RNA and (2'-5')oligoadenylate in the interferon-mediated inhibition of viral translation. Interferon; Mechanisms of production and action. Ed. R. M. Friedman—Amsterdam: Elsevier Scientific Publ. Co.- 1984.-3.-p.189–298.
[2]Eppstein D. A., Schryver B. B., Marsh Y. V. et al., Dephosphorylated core (2'-5')oligoadenylate exerts its antimitogenic effect through mechanisms different from the (2'-5') A-dependent endonuclease. J. Interferon Res.-1983, N 3.-p. 305–311.
[3]Montefiori David C., Sobol Robert W., Li Shi Wu, et al., Inhibition of human immunodeficiency virus type 1 reverse transcriptase and infection in vitro. Proc. Nat. Acad. Sci. USA.-1989.86, N 18.-C., p. 7191–7194.

SUMMARY OF THE INVENTION

One of the biochemical reactions initiated by interferon is the induction of (2'-5')oligoadenylate synthetase, which, due to the presence of double helical RNA polymerizes ATP in (2'-5')oligoadenylates with the general formula pppA (2'A)$_n$ where n=1–3. Experimental data show that this course of biochemical transformations contributes principally towards the antiviral effect of interferons and that pppA(2'A)$_n$ acts as the key mediator of this process At the same time pppA(2'A)$_n$ metabolizes actively in the cells under the influence of 2'-phosphodiesterase or 5'-phosphatases. In the last case, ppA(2'A)$_n$ converts to 5'-diphosphorylated "core" (2'-5')oligonucleotides (2'-5'A$_n$). These compounds exhibit a wide spectrum of biological effects: they inhibit the biosynthesis of DNA, RNA, and proteins (Johnston, Torrence, 1984)[4], they exhibit antimitogenic effect (Eppstein, Schryver, Marsh, et al., 1984)[5] and affect the activity of natural killer cells (Black, Henderson, Pfleiderer et al., 1984)[6].

[4]Johnston M. I., Torrence P. F., The role of interferon-induced proteins, double-stranded RNA and (2'-5')oligoadenylate in the interferon-mediated inhibition of viral translation. Interferon; Mechanisms of production and action. Ed. R. M. Friedman—Amsterdam: Elsevier Scientific Publ. Co.- 1984.-3.-p.189–298.
[5]Montefiori David C., Sobol Robert W., Li Shi Wu, et al., Inhibition of human immunodeficiency virus type 1 reverse transcriptase and infection in vitro. Proc. Nat. Acad. Sci. USA.-1989.86, N 18.-C., p. 7191–7194.
[6]Black P. L., Henderson E. E., Pfleiderer W. et al., (2'- 5')oligoadenylate trammer core and the cordycepin analog augment the tumoricidal activity of human natural killer cells. J. Immunol.-1984.-135, N 5.- p. 2773–2777.

It is of considerable interest that the 2'-5'A$_n$ (n=3) analogues possess various biological properties (Suhadolnik, Doetsch, Devash et al., 1983, Pfleiderer, Charubala, 1985)[7]. Based on the example of 2'-5'A$_3$ analogues which include well-known antimetabolites 9-(β-D-xylofuranosyl)adenine (2'-5')$A_2A^{l-epoxy}$ and 3'-deoxyadenosine [(2'-5')3'dA$_3$] in their structure, it has been shown that they are active against the Type I and II herpes virus. Under the influence of cellular phosphodiesterase, the trimers are hydrolyzed to the respective nucleoside-5'-monophosphates and nucleosides with their characteristic activity (Eppstein, Marsh, Schryver, 1983)[8].

On the other hand, it was shown quite persuasively in a series of papers that 2'-5'A$_3$ and their analogues exhibit their own characteristic activity as trimeric compounds (Johnston, Torrence, 1984)[9]. It should be stressed that these core trimers mimic many interferon effects in the cells (Imbach et al., U.S. Pat. No. 4,476,301 4/1982, Suhadolnik, Doetsch, Devash, et al., 1983[10] and Eppstein, Schryver, Marsh, et al, 1983)[11].

[7]Suhadolnik R. J., Doetsch P. W., Devash Y. et al., (2'-5')-Adenylate cordecypin trimer cores: metabolic stability and evidence for antimitogenesis without · 5'-rephosphorylation. J. Nucleosides Nucleotides.-1983.- 2.-N 4.-p351–366.
[8]Eppstein D. A., Marsh Y. V., Schryver B. B. Mechanism of antiviral activity of (Xylo A2'p)2XyloA. Virology.-1983. -131, N 2.-p. 341–354.
[9]Johnston M. I., Torrence P. F., The role of interferon-induced proteins, double-stranded RNA and (2'-5')oligoadenylate in the interferon-mediated inhibition of viral translation. Interferon; Mechanisms of production and action. Ed. R. M. Friedman—Amsterdam: Elsevier Scientific Publ. Co.-1984.-3.-p.189–298.

[10]Suhadolnik R. J., Doetsch P. W., Devash Y.-.et al., (2'-5')Adenylate cordecypin trammer cores: metabolic stability and evidence for antimitogenesis without 5'-rephosphorylation. J. Nucleosides Nucleotides.-1983.-2.N 4.-p351–366.

[11]Eppstein D. A., Marsh Y. V., Schryver B. B. Mechanism of antiviral activity of (Xylo A2'p)2XyloA. Virology.-1983. -131, N 2.-p. 341–354.

The advantage of using (2'-5')oligoadenylate analogues relates to their biological activity. They break down slowly under the influence of phosphodiesterase and maintain a long duration of activity in respect to T-lymphocytes (about 2 weeks). They are easily synthesized in large quantities using readily available synthetic chemical technique[12].

[12]Kvasyuk E. I., Kulak T. I., Khripach N. B. et al., Nucleotides XXIV; Preparative synthesis of trimeric (2'-5')oligoadenylic acid. Synthesis. -1987. -n 6. -p. 535–541.

Since they are analogues of natural products, they show little or no toxic activity and exhibit no undesirable effects on other important functions of the organism when used in immunosuppressive effective dosages. Normally, three component analogues of (2'-5')oligoadenylates, used singly or in a combination, are used with modifications in ribose positions 2' and 3' of the third terminal adenosine moiety.

Synthesized (2'-5')oligoadenylates have been found to be useful preparations as inhibitors of lymphocyte mitosis. In response to antigens, allogenic cells or natural mitogens, the lymphocytes enter the S-phase of division. The synthesis of deoxyribonucleic acid is initiated along with the first stage of the immune reaction.

During post-transplantation complications, in both autoimmune and tumor pathologies, it is necessary to inhibit DNA synthesis in order to stop the division of lymphocytes, especially of the T-helper and T-killer cells. The ability of low level concentrations of the chemically synthesized analogues of 2'-5'$A_3$ to inhibit the blast-transformation reaction under the influence of concanavalin A and lipopolysaccharides, and to suppress the division of T-helper and T-killer cells in the organism for an extended time, indicates their utility in the treatment of a variety of diseases.

This activity relates particularly to the treatment of diseases related to disturbance of T-cellular immunity: the autoimmune disorders, viral diseases, lymphocytic tumors and post-transplantation patients.

There have been discovered enzymes in the organism, namely the phosphodiesterases which hydrolyze 2'-5'$A_3$ to monomeric compounds (adenosone and its 5'-monophosphate) and which makes it impossible to utilize 2'-5'$A_3$ as immunosuppressant even at large concentrations, as we have shown in our in vivo experiments with monkeys, vide infra.

Therefore, we synthesized 2'-5'$A_3$ analogues which were believed to be more resistant to phosphodiesterase and selected out the most active inhibitors of lymphocyte mitoses on the basis of in vitro tests. The most promising analogues were (2'- 5')oligoadenylates containing 9-(2,3-anhydro-β-D-ribofuranosyl)adenine (2'-5')$A_2A_{r\text{-}epoxy}$ and 9-( 2,3-anhydro-β-D-lyxofuranosyl)adenine (2'-5')$A_2A_{l\text{-}epoxy}$. It was shown that both analogues are stable towards the action of snake venom phosphodiesterase (c. f., Example 3). For example, (2'-5')$A_2A_{r\text{-}epoxy}$ is 35-fold as resistant as its prototype 2'-5'$A_3$. These analogues manifested a much more marked action and differed from 2'-5'$A_3$ in their reaction to blast-transformation of lymphocytes stimulated by concanavalin A (Con A) and lipopolysaccharide (LPS). Con A stimulates primarily the division of T-lymphocytes while LPS affects β-lymphocytes.

DETAILED DESCRIPTION OF THE INVENTION

Figure 1:
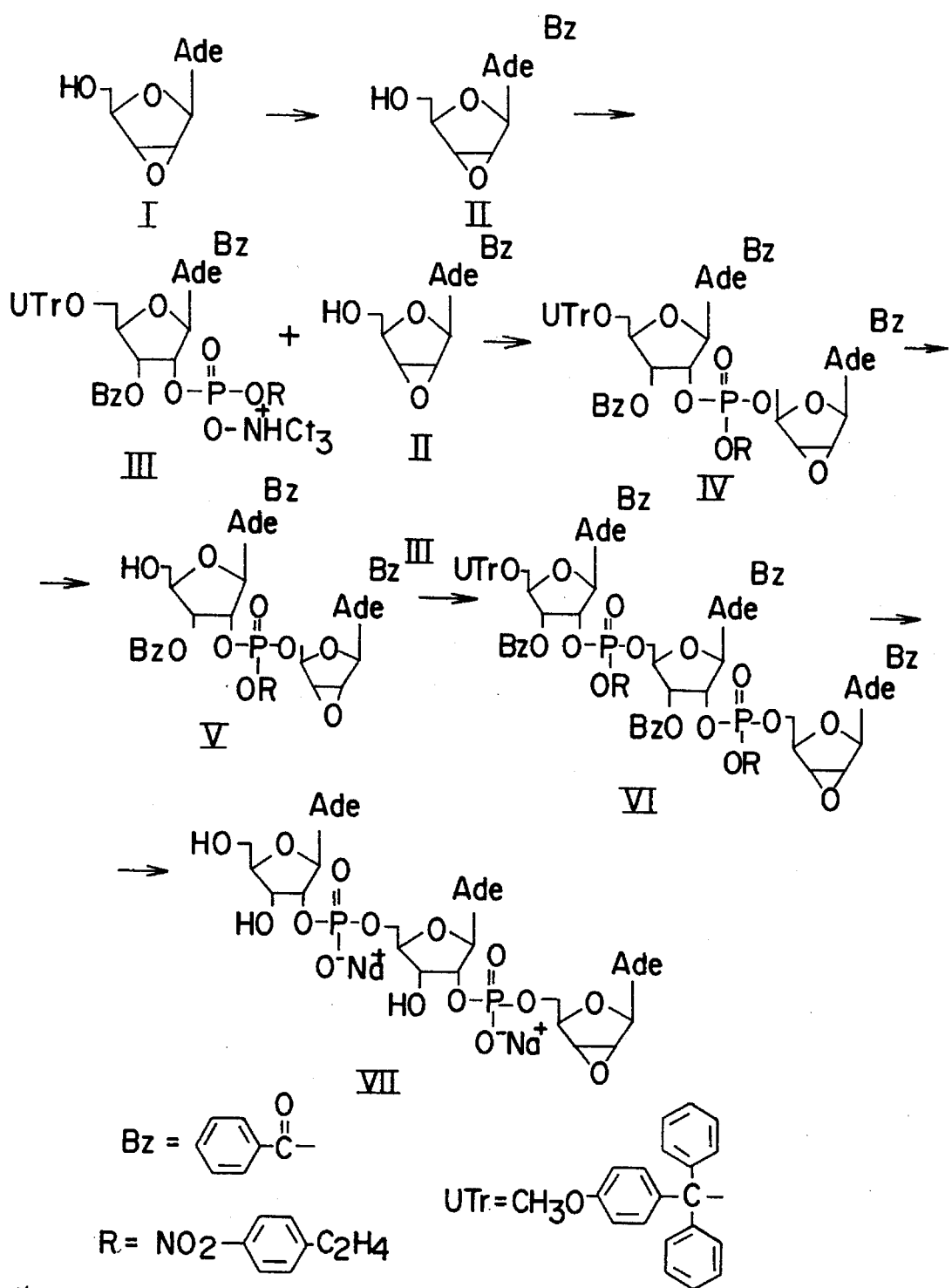
FIG. 1 is a schematic diagram for the synthesis of (2'-5')$A_2A_{r\text{-}epoxy}$.

In contrast to other immunosuppressors, the 2'-5'$A_3$ analogues act highly specifically. The data obtained allow the assumption that one of the analogues, (2'-5')$A_2A_{r\text{-}epoxy}$, suppresses selectively the proliferation of activated T-lymphocytes evoked by interleukin-II. Suppressing production of interleukin-II with T-helper lymphocytes, (2'-5')$A_2A_{r\text{-}epoxy}$ suppresses formation of T-killer cells. During the post-transplantation period, the (2'-5')$A_2A_{r\text{-}epoxy}$ stimulates somewhat the number of T-suppressors which assures the tolerance of the host immune system towards the allotransplant.

In contrast to the widely used cyclosporine, (2'-5')$A_2A_{r\text{-}epoxy}$ does not suppress the production of γ-interferon. By stimulating the number of α- and γ-interferons in the lymphocytes, (2'-5')$A_2A_{r\text{-}epoxy}$ supports high anti-viral and antimicrobial status of the patients after transplantation.

All known immunosuppressors (cyclopeptides, corticosteroids, antimetabolites ) suppress most of the immunocompetent cells, weakening the immune system of the patient in the struggle with infection during the post transplantation period.

Acting specifically only to have -effect on the suppression of the number of T-killer and T-helper cells, (2'-5')$A_2A_{r\text{-}epoxy}$ stimulates, in a compensatory fashion, the antiviral and antimicrobial functional mechanisms of the immune system protecting the weakened organism from infection during the post-transplantation period.

In the in vivo experiments the principal difference between the actions of the prototype 2'-5'$A_3$ and the proposed analogues (2'-5')$A_2A_{r\text{-}epoxy}$ and (2'-5')$A_2$ $A^{l\text{-}epoxy}$ became manifested. It was found that (2'-5')$A_3$ at concentrations proposed by Kimchi et al., 1980, displayed no immunosuppressive activity; in fact it stimulated the number of T-killers and T-helpers in monkeys by 50% after IV injection for four days.

We have shown that (2'-5')$A_2A_{r\text{-}epoxy}$ and (2 - 5')$A_2A^{l\text{-}epoxy}$ analogues possess strong immunosuppressive activity specifically against T-killers and T-helpers. A single IV injection of (2'-5')$A_2A_{r\text{-}epoxy}$ suppresses the number of T-killers and T-helpers by 50% in 48 hours. This effect is increased by 2 to 4 times over the next two weeks (c. f., Example 6).

Comparative analysis of the activity of both analogues showed that (2'-5')$A_2A_{r\text{-}epoxy}$ A was more resistant to phosphodiesterase than (2'-5')$A_2A^{l\text{-}epoxy}$ and suppressed more actively the number of T-killer and T-helpers.

Therefore in further experiments we used (2'-5')$A_2A_{r\text{-}epoxy}$ as the immunosuppressor in kidney transplantations in animals. It has been shown that IV injections of (2'-5')$A_2A_{r\text{-}epoxy}$ to rabbits at a dose of 5 µg/kg body weight assured normal functioning of the transplanted kidney for a period of 3 months. The rabbits were alive even on the transplanted kidney alone after subsequent removal of their healthy kidney, which initially functioned along with the transplanted organ. The experiments showed that lymphocyte blast-transformation in post-transplanted rabbits stimulated with Con A was suppressed almost 10-fold.

Experiments on monkeys showed that IV administration of (2'-5')$A_2A_{r\text{-}epoxy}$ every 48 hours at a concentration of 50 µg/kg assures immunosuppression, protects the transplant from rejection, and renews normal functioning of the transplanted kidney. The number of T-helper-and T-killer cells during the most critical first two post-surgical weeks was suppressed 2- to 3-fold, retaining a 30% level of the normal value.

Changing the schedule of the IV injection of $(2'-5')A_2A_{r-epoxy}$ doses of 50 µg/kg to 2, 6, 12 days and then every sixth day, transplanted kidney resumes and maintains its normal functions. The number of T-helpers and T-killers during the post-transplantation period remains normal for two critical weeks. After that both fall below the normal level.

Thus, a dose dependence was discovered between the action of $(2'-5')A_2A_{r-epoxy}$ and the number of T-killer and T-helper cells in the blood of transplanted animals. The optimal concentration of $(2'-5')A_2A_{r-epoxy}$ is in the range of 5 . 50 µg/kg body weight of the experimental animal. Depending on the administration frequency, this value may range from 0.01 to 1000 µg/kg body weight.

However, the best criterion for the selection of the dose and administration schedule should be based on clinical indices: first of all the number of T-killer and T-helper cells which should not rise and could fall only within 50% of the normal level during the first 2-3 post-transplantation weeks, while staying at the lower limit of the normal reading during the post-transplantation period.

$(2'-5')A_2A_2A$ is recommended as an immunosuppressor for transplantation of kidneys, heart, lungs, bone marrow and other organs. $(2'-5')A_2A_2A$ may be used in rescue treatment of transplant rejection. It could also be used for prophylaxis of transplant rejection after bone marrow transplantation and in treatment of the graft vs. host disease.

The present invention will be illustrated with reference to the following Examples, which are to be construed in a non-limitative manner and modifications obvious to a person skilled in this art are considered to be within the scope of the invention which is taught and claimed.

CHEMICAL SYNTHESIS OF (2'-5') OLIGOADENYLATE ANALOGUES

EXAMPLE 1

Adenylyl (2'-5')adenylyl (2'-5')- 9-(2,3-anhydro-β-D-ribofuranosyl) adenine disodium salt $[(2'-5')A_2A_{r-epoxy}]$.

TABLE 1

The following compounds are used in the new synthesis scheme of adenylyl(2'–5')adenylyl(2'–5')-9-(2,3-anhydro-β-D-ribofuranosyl adenine (disodium salt) [Reagent I]:

I. 9-(2,3-anhydro-β-D-ribofuranosyl)adenine
II. 6-N-Benzoyl-9-(2,3-anhydro-β-D-ribofuranosyl)adenine
III. 6-N,3'-O-Dibenzoyl-5'-O-monomethoxytrityladenosine-2'-[2-(4-nitrophenyl)-ethyl]-phosphate
IV. 6-N,3'-O-Dibenzoyl-5'-O-monomethoxytrityladenylyl-{2'-[O(P)-/2-(4-nitrophenyl)-ethyl/]-5'}-6-N-benzoyl-9-(2,3-anhydro-β-D-ribofuranosyl)adenine
V. 6-N,3'-O-Dibenzoyladenylyl-{2'-[O(P)-/2-(4-nitrophenyl)-ethyl/]-5'}-6-N-benzoyl-9-(2,3-anhydro-β-D-ribofuranosyl)-adenine
VI. 6-N,3'-O-Dibenzoyl-5'-O-monomethoxytrityladenylyl-{2'-[O(P)-/2-(4-nitrophenyl)-ethyl/]-5'}-6-N-3'-dibenzoyladenylyl-{2'-[O(P)-/2-(4-nitrophenyl)-ethyl/]-5'}-6-N-benzoyl-9-(2,3-anhydro-β-D-ribofuranosyl)adenine
VII. 6-N,3'-O-Dibenzoyladenylyl-2'-{O(P)-/2-(4-nitrophenyl)-ethyl/}-6-N,3'-O-dibenzyol-(2'-{O(P)-/2-(4-nitrophenyl)-ethyl/}-5')-6-N-benzoyl-9-(2,3'-anhydro-β-D-ribofuranosyl)adenine
VIII. Adenylyl(2'-5')adenylyl(2'-5')-9-(2,3-anhydro-β-D-ribofuranosyl)adenine (disodium salt)

1.1. 6-N-Benzoyl-9-( 2,3-anhydro-β-D-ribofuranosyl)adenine (II*).

A mixture of 80 g (3.21 mM) of nucleoside I. (see Table I) in 12 ml of hexamethyldisilazane (HMDS) and 10 mg of ammonium chloride is boiled for 2 hours until complete dissolution of the compound. The reaction mixture is evaporated, the residue is dissolved in 5 ml of pyridine, the solution is cooled to 0° C. and 0.78 ml (0.95 g; 6.74 mM) of benzoyl chloride is added to it. Twenty hours later, 5 ml of 10% aqueous ammonia solution is added to the reaction mixture and 7 minutes later the solution is evaporated. The residue is chromatographed on silica gel L (Chemapoe, Czechoslovakia) 40/100 µ(100 cm³), the products being eluted with chloroform, then with 9:1 mixture of chloroform-methanol. Fractions, containing the compound II are combined and evaporated. The residue is crystallized from ethanol. 1.04 g (91.7%) of nucleoside II is obtained; its melting point was 185°–188° C. UV-spectrum in methanol, λmax., nm (1 g E): 234 (4.18), 261 sh (4.16), 282 (4.36).

NMR-spectrum in deuterodimethylsulfoxide, δ, TMS ppm: 11.20 s (IH, NH2), 8.78 and 8.64 s by IH (H-2, H-8), 8.08–7.52 m (5H, OBz), 6.36 s (IH, H-I'), 5.06 m (IH, 5'-OH), 4.56 d (IH, H-2', J 2'3'=3.0 Hz), 4.26 d (IH, H-3', J 3'2'=3.0 Hz), 4.24 dd (IH, H-4', J 4', 5'=J 4', 5"=4.8 Hz), 3.58 m (2 H, H-5', H-5").

Analysis found, %: C 57.92; H 4.23; N 19.74; Calculated for $C_{17}H_{15}N_5O_4$., %: C 57.70; H 4.28; N 19.82.

1.2. Adenylyl(2'-5')adenylyl(2'-5')-9-( 2,3-anhydro-β-D-ribofuranosyl)-adenine, disodium salts (VII)

0.50 g (7.20 mM) of tetrazole and 0.73 g (2.40 mM) of 2,4,6-triisopropylbenzene sulfone chloroide are added to the mixture of 0.35 g (1.00 mM) of nucleoside II and 1.29 g (1.20 mM) of diesther III in 10 ml pyridine. The reaction mixture was stirred for 16 hours, diluted to 200 ml with chloroform and extracted with (2+70 ml) 0.05 M phosphate buffer, pH 7.0. The organic layer was-separated, dried with anhydrous sodium sulfate, evaporated and the residue=was chromatographed on silica gel L 40/100 (150 cm³), the reaction products were eluted with chloroform. Fractions, containing the compound IV, were combined and evaporated. 1.12 g (86%) of the blocked dimer IV was obtained.

1.12 g (0.86mM) of the compound IV was dissolved in 69 ml of 2% of R-toluene sulfonic acid solution in a 7:3 mixture of methylene chloride-methanol. Ten minutes later, the resultant solution was diluted with chloroform to 200 ml volume and extracted with 3×100ml of phosphate buffer, pH 7.0. The organic layer-was separated, dried with anhydrous sodium sulfate and evaporated. The residue was chromotographed on silica gel L 40/100 (150 cm³); the reaction products were eluted in a concentration gradient of methanol in chloroform (from 0 to 5 percent volume, the total volume being 1 l). Fractions containing the compound V, were combined and evaporated to yield. 0.81 g (91.2%) of detritylated dimer V.

0.81 g (0.78 mM) of dimer V and 1.01 g (0.94 mM) of diesther III were condensed in 7.8 ml of pyridine in the presence of 0.39 g (5.61 mM) of tetrazole and 0.57 g (1.87 mM) of 2,4,6-triisopropylbenzene sulfone chloride for 16 hr. The reaction mixture was treated and chromatographed, in the same manner as dimer IV. 1.45 g (93.1%) of blocked trimer VI was obtained.

1.45 g (0.73mM) of the compound VI was dissolved in 58 ml of 2% of p-toluene sulfonic acid solution in a 7:3 mixture of methylene chloride- methanol. Ten minutes later, the mixture was diluted with chloroform up to 150 ml and was extracted with 3×70 ml portions of phosphate buffer, pH 7.0. The organic layer was separated, dried with anhydrous sodium sulfate and evaporated. The residue was dissolved in 220 ml of 0.5 M 1,8-diazabicyclo-/5,4,0/-undec-7-ene (DBU) solution in pyridine and left standing for 20 hours. 110 ml of a 1 M solution of acetic acid in pyridine was added to the above solution, and then it was evaporated; the residue was evaporated with addition of pyridine (3×30ml). The residue, obtained after evaporation, was dissolved in 200 ml of 25% solution of aqueous ammonia, left standing for 20 hours and then evaporated. The residue was chromatographed on DEAE-cellulose in the $HCO_3^-$ form (300 cm$^3$). The column was eluted with the solution of triethylammonium bicarbonate in a concentration gradient from 0.01 to 0.20 M. Fractions, containing the trimer VII, were combined and lyophilized. 0.62 g (77%) of adenine adenylyl(2'-5')adenylyl (2'-5')-9-(2,3-anhydro-β-D-ribofuranosyl)adenine (VII) was obtained in the form of triethylammonium salt. The compound was converted from the triethylammonium salt to the sodium salt by the action of sodium iodide in acetone on the triethylammonium salt solution of VII in methanol. UV-spectrum in water, λmax., nm (1 g E): 259 (4.57).

NMR-spectrum in $D_2O$, δ, TMS ppm, tert-butanol being used as the internal standard: 6.93; 6.86; 6.85; 6.61; 6.59; 6.46—singlets by IH (H-2, H-8), 4.88 s (IH, H-I'), 4.88 d (IH, H-I', J I', 2'=4.2 Hz), 4.50 d (IH, H-I', J I', 2'=2.4 Hz).

The total yield of trimer VII, calculating on the basis of adenosine, used for obtaining the anhydro derivative II, is equal to 50.5%. Moreover, the presence of only one benzoyl group in 6-N-position of the compound II has a positive effect on its stability, which leads, ultimately, to higher yield of the end product.

EXAMPLE 2

Adenylyl (2'-5')adenylyl (2'-5')-9-( 2,3-anhydro-β-D-lyxofuranosyl) adenine disodium salt [(2'-5')$A_2A^{I-epoxy}$].

2.1. 6-N-Benzoyl-9-( 2,3-anhydro-β-D-lyxofuranosyl)adenine (II*).

0.40 ml (3.17 mM) of trimethylchlorosilane was added to the solution of 0.10 g (0.40 mM) of nucleoside 1 in 2.8 ml of pyridine and the reaction mixture was stirred for 4 hours.

TABLE 2

The following compounds are used in the new synthesis scheme of adenylyl(2'-5')adenylyl(2'-5')-9-(2,3-anhydro-β-D-lyxofuranosyl)adenine (disodium salt):

I*. 9-(2,3-Anhydro-β-D-lyxofuranosyl)adenine
II. 6-N-Benzoyl-9-(2,3-anhydro-β-D-lyxofuranosyl)adenine
III. 6-N,3'-O-Dibenzoyl]-5'-O-monomethoxytrityladenosine-2'-[2-(4-nitrophenyl)-ethyl]-phosphate
IV. 6-N,3'-O-Dibenzoyl-5'-O-monomethoxytrityladenylyl-{2'-[O(P)-/2-(4-nitrophenyl)-ethyl/]-5'}-6-N-benzoyl-9-(2,3'-anhydro-β-D-lyxofuranosyl)adenine
V. 6-N,3'-O-Dibenzoyladenylyl-{2'-[O(P)-/2-(4-nitrophenyl)-ethyl/]-5'}-6-N-benzoyl-9-(2,3'-anhydro β-D-lyxofuranosyl)-adenine
VI. 6-N,3'-O-Dibenzoyl-5'-O-monomethoxytrityladenylyl-{2'-[O(P)-/2-(4-nitrophenyl)-ethyl/]-5'}-6-N,-3'-O-dibenzoyladenylyl-{2'-[O(P)-/2-(4-nitrophenyl)-ethyl/]-5'}-6-N-benzoyl-9-(2,3-anhydro-β-D-lyxofuranosyl)adenine
VII. 6-N,3'-O-Dibenzoyladenylyl-2'-{O(p)-/2-(4-nitrophenyl)-ethyl/]-5'}-6-N-3'-O-dibenzoyladenylyl-{2'[O(p)-/2-(4-nitrophenyl)ethyl/]-5'}-6-N-benzoyl-9-(2,3'-anhydro-β-D-lyxofuranosyl)adenine
VIII. Adenylyl(2'-5')adenylyl(2'-5')-9-(2,3-anhydro-β-D-lyxofuranosyl)adenine (disodium salt)

The mixture was cooled to 0° C., 0.11 g (0.09 ml; 0.80 mM) of benzoyl chloride was added, and the reaction mixture was allowed to warm to room temperature with stirring for 40 minutes, after which it was cooled to 0° C., 0.6 ml of water was added, followed 5 minutes later by 0.8 ml of 25% aqueous ammonia solution.

After stirring for 6 minutes, the reaction mixture was evaporated. The residue, was chromatographed on a silica gel column (100 cm$^3$); the reaction products were eluted with the methanol concentration gradient in chloroform (0–10 volume %, the total volume being 1 l). Fractions, containing benzoate II were combined and evaporated. The residue was crystallized from ethanol. 0.12 g (84%) of nucleoside II was received; temperature of melting point 163°–165° C.

UV-spectrum in methanol, λmax., nm (1 g E) : 234 (4.18), 281 (4.26).

NMR-spectrum in deuterodimethylsulfoxide, δ, TMS ppm: 8.80 and 8.38 s by IH (H-2, H-8), 8.08–7.53 m (5 H, Obz), 6.45 s (IH, H-I'), 5.05m (IH, OH-5'), 4.36 d (IH, H-2', J 2', 3'=2.4 Hz), 4.18 m (2 H, H-3 , H-4'), 3.63 m (2 H, H-5', H-5")

2.2. Adenylyl (2'-5')adenylyl (2'-5')-9-( 2,3-anhydro-β-D-lyxofuranosyl)adenine, disodium salt (VIII)

59 mg (0.84 mM) of tetrazole was added to the solution of 35 mg (0.10 mM) of nucleoside II and 151 mg (0.14 mM) of diether III in 1 ml of pyridine; following the dissolution of the former, 85 mg (0.28 mM) of 2,4,6-triisopropylbenzene sulfonyl chloride was added. The reaction mixture was left standing for 20 hours, then it was diluted up to 100 ml with chloroform and extracted with 0.05 M TEAB solution (50 ml); the organic layer was separated, dried with anhydrous sodium sulfate and evaporated. The residue, containing dinucleoside monophosphate IV, was treated with 2% solution of p-toluene sulfonic acid in a 7:3 mixture of methylene chloride-methanol. Fifteen minutes later the solution received was diluted with chloroform up to 100 ml, extracted with 0.05 M of TEABsolution (2×50ml), the organic layer was separated, dried and evaporated. The residue was chromatographed on the silica gel column (50 cm$^3$), the products were eluted with chloroform (500 ml). Fractions, containing dinucleoside monophosphate V, were combined and evaporated. After precipitation in hexane 79 mg (77%) of compound V was received in the form of an amorphous powder.

Trinucleoside diphosphate VI was obtained by condensation of 79 mg (0.076 mM) of dimer V and 114 mg (0.106mM) of diester III in the presence of 64 mg (0.212 mM) of 2,4,6-triisopropylbenzene sulfonyl chloride and of 45 mg (0.636 mM) of tetrazole followed by treatment of the reaction mixture, as it was described for obtaining the compound IV. Trinucleoside diphosphate VI was dissolved in 8.5 ml of 2% p-TsOH solution in 7:3 mixture of methylene chloride-methanol. Fifteen minutes later the reaction mixture was treated, as was described above for the compound V, and chromatographed on the silica gel column (50 cm$^3$); the reaction products eluted with the methanol concentration gradient in chloroform (0–2 volume %, the total volume was 500 ml.). Fractions, containing the compound VII were combined and evaporated. After precipitation in hexane 89 mg (68%) of trinucleoside diphosphate VII was obtained.

16.5 ml of 0.5 M DBU in pyridine was added to 89 mg (0.052 mM) of trimer VII. After 18 hours, 8.3 ml of 1 M acetic acid solution in pyridine was added, then the solution was evaporated. The residue was evaporated with pyridine (2×15 ml). After evaporation the residue was dissolved in 20 ml of the concentrated aqueous ammonia solution, the reaction mixture stood for 18 hours and was evaporated. The residue was chromatographed on the DEAE-cellulose SS-23 column in the form of $HCO_3^-$, the products being eluted with the concentration gradient of triethylammonium bicarbonate aqueous solution (0.001–0.2 M, the total volume 1 l). The fractions, containing deblocked trimer VIII, were combined and lyophilized. Forty-three mg (73%) of compound VIII was obtained in the form of a triethylammonium salt. The compound was transformed to sodium salt by the action of triethylammonium salt solution in methanol with sodium chloride solution in acetone.

UV-spectrum in water, λmax., nm (1 g E): 260 (4.54).

NMR-spectrum in $D_2O$, δ, TMS ppm, tert-butanol being the internal standard: 6.97; 6.92; 6.86; 6.83; 6.82; 6.58-singlets by IH (H-2, H-8); 4.87 d (IH, H-I', JI', 2'=4.2 Hz); 4.86 s (IH, H-I'); 4.76 d (IH, H-I', JI', 2'=3.6 Hz).

EXAMPLE 3

Determination of (2'-5')oligoadenylates and analogues stability to the action of snake venom phosphodiesterase Upon entering an organism $2'-5'A_3$ and the analogues are quickly hydrolyzed to monomeric compound(s). Prior to administration of $2'-5'A_3$ analogues in vivo to animal, it was considered necessary to determine their stability towards snake venom phosphodiesterase in comparison to the parent $2'-5'A_3$.

The solution of 3 μg of the snake venom phosphodiesterase (Boehringer Mannheim cat. No. 108260) in 30 μl of 0.1 M Tris HCl buffer, containing 0.002 M $MgCl_2$ (pH 8.78) is added to the solution of $4-5 \cdot 10^{-7}$ M trimer in 100 μl of the same buffer. The solution was left standing at 20° C. At regular intervals, 10 μl samples were taken, heated at 90° C. for 1 minute and preparative thin layer chromatography was performed on the Silufole™ plates, using a 7:1:2 mixture of isopropanol:aqueous ammonia:water.

The spot, corresponding to the initial trimer, was cut out, the substance was extracted with 2 ml of 0.5% solution of the dodecylsulfate sodium salt solution for 2 hours, and the optical density of the solution was determined at 260 nm. The time during which the optical density of the solution of the initial compound decreased by 50% was determined. Thus, T½ for $2'-5'A_3$ was shown to be 27 minutes, for $(2'-5')A_2A^{l\text{-}epoxy}$ it was 10.5 hours and for $(2'-5')A_2A_{r\text{-}epoxy}$ it was 16.0 hours.

The experiments have shown that $2'-5'A_3$ was extremely sensitive to the action of phosphodiesterase while its analogues $(2'-5')A_2A_{r\text{-}epoxy}$ and $(2'-5')A_2A^{l\text{-}epoxy}$ were significantly more resistant towards hydrolysis by phosphodiesterase. This demonstrates that these analogues are more resistant to metabolism within an organism wherein .phosphodiesterase is present.

EXAMPLE 4

Estimation of Lymphocyte Proliferation

The immune reactions in an organism begins with the division of lymphocytes. In vitro investigation of the lymphocyte blast-transformation reaction under the influence of mitogens makes it possible to use this model system to select chemically synthesized $2'-5'A_3$ analogues which suppress division of lymphocytes. Using Concanavalin A and lipopolysaccharide as mitogens, the effect of analogues on the division of T- and β-lymphocytes may be investigated.

CBA mice 8–10 weeks old were used for these experiments. A suspension of mouse splenocytes were obtained by gently teasing spleens with forceps. Lymphocytes cultivated in flat-bottomed 96-well plates (Linbro) in RPMI-1640 medium (Flow Lab.) were supplemented with 2 mM 1-glutamine, 10 μg/ml gentamicin, $10^{-5}$ M 2-mercaptoethanol and 10% heat inactivated fetal calf serum (Flow Lab). Cultures were maintained in 5% $CO_2$ at 37° C. One μCi of $^3$H-thymidine (Isotop®) was added to each well 4 hours before the end of the incubation period. Incorporation of $^3$H-thymidine into cellular DNA was determined by liquid scintillation counting using standard techniques. Oligoadenylate was added to the medium at the beginning of culturing to achieve the final concentration.

Analysis of the data-shows that $2'-5'-A_3$ and its analogues $(2'-5')A_2A_{r\text{-}epoxy}$ and $(2'-5')A_2A^{l\text{-}epoxy}$ act as inhibitors of lymphocyte blast-transformation reaction. The three preparations have been shown to be effective both in the case of Concanavalin A (Con A), and in the case of lipopolysaccharide (LPS). (Con A being a mitogen for T-lymphocytes and LPS being a mitogen for β-lymphocytes). Tables 3, 4, and 5 show the different actions of the three investigated preparations. The parent $2'-5'A_3$ suppresses the division of β-lymphocytes more effectively, while the $(2'-5')A_2A_{r\text{-}epoxy}$ suppresses the T-lymphocyte division to a greater extent, but shows a weaker effect of the division of β-lymphocytes. The reaction shows a concentration dependence (Tables 4 and 5).

TABLE 3

Comparative Analysis of In Vitro Blast-transformation of Murine Lymphocytes Treated with (2'-5')oligoadenylates at a concentration of $5 \times 10^{-6}$ M.

| | | DNA synthesis at [$^3$H]-thymidine [incorporated counts/min.] | | |
|---|---|---|---|---|
| | Con- | Preparation | | |
| Mitogen | trol | $2'-5'A_3$ | $(2'-5')A_2A_{r\text{-}epoxy}$ | $(2'-5')A_2A^{l\text{-}epoxy}$ |
| Con A (5 μg/ml) | 22,296 | 18,934 | 16,399 | 15,749 |
| LPS (0.1 μg/ml) | 27,133 | 1,588 | 21,464 | 10,828 |

TABLE 4

In Vitro Blast-transformation of Murine Lymphocytes Treated with $(2'-5')A_2A_{r\text{-}epoxy}$ and Mitogens

| | DNA synthesis at [$^3$H]-thymidine [incorporated counts/min.] $(2'-5')A_2A_{r\text{-}epoxy}$ Concentration* (M) | | | | | | |
|---|---|---|---|---|---|---|---|
| Control | $1 \times 10^{-5}$ | $5 \times 10^{-6}$ | $5 \times 10^{-7}$ | $5 \times 10^{-8}$ | $5 \times 10^{-9}$ | $5 \times 10^{-10}$ | $5 \times 10^{-11}$ |
| Con A (5 μg/ml) 5,428 | 4,172 | 1,733 | 3,865 | 5,383 | 1,599 | 777 | 5,271 |
| LPS (0.1 μg/ml) 10,766 | — | 7,665 | 6,018 | 4,767 | 7,348 | 672 | — |

TABLE 5

In Vitro Blast-transformation of Murine Lymphocytes
Treated with $(2'-5')A_2A_{r\text{-}epoxy}$ and Mitogens

| | DNA synthesis at [$^3$H]-thymidine [incorporated counts/min.] $(2'-5')A_2A_{r\text{-}epoxy}$ Concentration (M) | | | | | |
|---|---|---|---|---|---|---|
| Control | $1 \times 10^{-5}$ | $5 \times 10^{-6}$ | $5 \times 10^{-7}$ | $5 \times 10^{-8}$ | $5 \times 10^{-9}$ | $5 \times 10^{-10}$ |
| Con A (5 µg/ml) 5,108 | 2,960 | 4,732 | 2,237 | 1,355 | 6,915 | 1,425 |
| LPS (0.1 µg/ml) 5,513 | — | 131 | 292 | 655 | 3,342 | 1,213 |

EXAMPLE 5

Duration of $(2'-5')A_2A_{r\text{-}epoxy}$ Activity in the Blood of Rabbits

In order to study $(2'-5')A_2A_{r\text{-}epoxy}$ pharmacodynamics, the radioimmune and fluoroimmune techniques were developed for its detection in tissue. The level of the natural compound $2'-5'A_3$ in the blood plasma was shown to be equal to $10^{-12}$ M, and in the blood cells it was shown to be $10^{-11}$ M. Ten minutes following one injection of $(2'-5')A_2A_{r\text{-}epoxy}$ at concentration of 10 µg/kg of the body weight of the rabbit,- a 10-fold decrease of the level of natural compounds was noted in the blood plasma and a 10-fold increase of their concentration in the blood cells. A subsequent 20-day study of these indices showed the preservation of the compounds of this class at natural basal level changes for 2 weeks, reaching the normal level only on the 15th day.

Thus, these findings showed that one injection of $(2'-5')A_2A_{r\text{-}epoxy}$ ensures its effect on the organism for two weeks.

EXAMPLE 6

(2'-5')Oligoadenylate and two analogues Effect on the Immune System of Monkeys

Immunosuppressive activity of the prototype $2'-5'A_3$ and two analogues $(2'-5')A_2A_{r\text{-}epoxy}$ and $(2'-5')A_2A^{l\text{-}epoxy}$ were investigated in monkeys. The experiments were performed on 4 year-old Macaque Rh. monkeys. The levels of the principal subpopulations of T-lymphocytes, IgA, IgG, IgM and the amount of α- and γ-interferon and interleukin II after administration (2'-5')olygoadenylate and its analogies at the concentration of 50 and 25 µg/kg of the body weight was investigated.

IMMUNOGLOBULIN DETERMINATION

Serum levels of IgG, IgA, IgM were determined by radial immunodiffusion using antisera against human immunoglobulin A, M, G. The amount of interferon and interleukine-II were determined by the method of Lopez-Botet M. et al., 1982.

FLOW CYTOFLUOROGRAFIC ANALYSIS OF LYMPHOCYTE SUBSETS

Blood samples (100 µl of whole blood) were placed into a 12×17 tube. To these cells 20 µl of purified monoclonal antibodies were added with specificity for human cytotoxic/suppressor cells anti-Leu-2a (CD8), human helper/inducer anti-Leu-3a (CD4) and FITC conjugated monoclonal antibodies with specificity for natural killer cells-anti-Leu11c (CD16) (Becton Dickinson, San Jose). After 30 minutes incubation on ice, the cells were washed once and 20 µl of goat-antimouse chain phycoerythrin (Sigma P1286) conjugate were added to the tube with anti-Leu-2a and anti-Leu-3a monoclonal antibodies.

After erythrocyte lysing with FACS lysing solution (Becton Dickinson, San Jose) the cells were analyzed on FACScan flow cytometer (Becton Dickinson, San Jose) with scatter gate set on lymphocyte fraction. Experimental results are reported in Table 6–10 and 14.

TABLE 6

Effect of Single Intravenous Administration of $(2'-5')A_2A_{r\text{-}epoxy}$ on the Immune System of Macaque Rh. Monkeys at a Dose of 25 µg/kg

| Type of Assay | Days following the administration of $(2'-5')A_2A_{r\text{-}epoxy}$ | | | | | | |
|---|---|---|---|---|---|---|---|
| | 0 | 1 | 2 | 4 | 8 | 12 | 21 |
| IgG (g/l) | 7.5 | 7.4 | 5.2 | — | 14.5 | — | 14.48 |
| IgA (g/l) | 2.8 | 2.0 | 1.1 | — | 0.53 | — | 0.38 |
| IgM (g/l) | 0.5 | 0.6 | 1.0 | — | 1.41 | — | 1.2 |
| T-helpers (%) | 16 | 20 | 10 | 4 | 5.3 | 7 | 23 |
| T-suppressor (%) | 47 | 40 | 21 | 11 | 11 | 14 | 46 |
| T-killers (%) | 9.9 | 12 | 8 | 4 | 4 | 4 | 6.4 |

TABLE 7

Effect of Single Intravenous Administration of $(2'-5')A_2A_{r\text{-}epoxy}$ on the Immune System of Macaque Rh. Monkeys at a Dose of 50 µg/kg

| Type of Assay | Days following the administration of $(2'-5')A_2A_{r\text{-}epoxy}$ | | | | | | |
|---|---|---|---|---|---|---|---|
| | 0 | 1 | 2 | 4 | 8 | 12 | 21 |
| IgG (g/l) | 9.6 | 7.8 | 15.0 | — | 14.8 | — | 13.2 |
| IgA (g/l) | 2.8 | 2.7 | 0.8 | — | 0.9 | — | 0.38 |
| IgM (g/l) | 0.6 | 0.5 | 1.1 | — | 0.9 | — | 0.78 |
| T-helpers (%) | 30 | 29 | 15 | 1.2 | 5.0 | 7.0 | 30.6 |
| T-suppressors (%) | 43 | 31 | 19 | 12 | 7.4 | 13 | 44 |
| T-killers (%) | 12 | 9 | 7 | 1.5 | 4.4 | 9 | 19.3 |

The data shows that $(2'-5')A_2A_{r\text{-}epoxy}$ inhibits subpopulation of T-lymphocytes (Table 6 and 7). As indicated, a single intravenous injection of $(2'-5')A_2A_{r\text{-}epoxy}$ results in a 2- to 4-fold reduction of the subpopulation of T-lymphocytes. -Upon this basis, we identified a relationship between the quantity of injected preparation and the quantity of T-helper and T-killer cells.

TABLE 8

Effect of Single Intravenous Administration $(2'-5')A_2A^{l\text{-}epoxy}$ on the Immune System of Macaque Rh. Monkeys at a Dose of 25 µg/kg

| Type of Assay | Day before injection (control) | Days following the preparation administration | |
|---|---|---|---|
| | | 2 | 4 |
| T-helpers (%) | 26.2 | 27 | 25.3 |
| T-suppressors (%) | 53.1 | 44 | 43.4 |

TABLE 9

Effect of Single Intravenous Administration $(2'-5')A_2A^{l\text{-}epoxy}$ on the Immune System of Macaque Rh. Monkeys at a Dose of 50 µg/kg

| Type of Assay | Day before injection (control) | Days following the preparation administration | |
|---|---|---|---|
| | | 2 | 4 |
| T-helpers (%) | 22 | 20.5 | 18.4 |
| T-suppressors (%) | 42 | 44 | 43.4 |

The data show that $(2'-5')A_2A^{l\text{-}epoxy}$ manifested also immunosuppressive activity at the concentrations studied. However, its action with respect to the T-helpers and T-suppressors was considerably lower than that exhibited by $(2'-5')A_2A_{r\text{-}epoxy}$ (Table 8 and 9).

It has been shown that the analogues $(2'-5')A_2A_{r\text{-}epoxy}$ and $(2'-5')A_2A^{l\text{-}epoxy}$ exhibit immunosuppressive activity in the in vivo experiments. At two concentrations 25 and 50 µg/kg body weight, the preparation $(2'-5')A_2A_{r\text{-}epoxy}$ suppresses significantly the number of T-lymphocytes in blood after only 48 hours and maintains them at normal level for two weeks. It has been shown that, at these concentrations, $(2'-5')A_2A_{2r\text{-}epoxy}$ suppresses the number of T-suppressor cells, as well. It appears that the concentration of 25 µg/kg body weight represents the upper limit for its use other than in a transplantation situation. We have shown also that, at the concentration of 50 µg/kg $(2'-5')A_2A_{r\text{-}epoxy}$ the drug stimulates the number of T-suppressor cells in transplanted monkeys.

We can compare the action of $(2'-5')A_2A_{r\text{-}epoxy}$ shown in Tables 6 and 7 with their prototype $2'-5'A_3$ in vivo. The results of experiments with $2'-5'A_3$ are reported in Table 10.

TABLE 10

Effect of Single Intravenous Administration $2'-5'A_3$ on the Immune System of Macaque Rh. Monkeys at a Dose of 500 µg/kg

| Type of Assay | Day before injection (control) | Days following the preparation administration | |
|---|---|---|---|
| | | 2 | 4 |
| T-helpers (%) | 22.1 | 32.3 | 37.2 |
| T-suppressors (%) | 33.2 | 36.0 | 44.2 |
| T-killers (%) | 8 | 12 | 12 |

The results show that $2'-5'A_3$ is different from $(2'-5')A_2A_{r\text{-}epoxy}$ in its action on T-cell immunity. It is shown that a single intravenous injection of $(2'-5')A_2 A_{r\text{-}epoxy}$ increases in about 50% the quantity of the subpopulation of T-helpers and T-killers, which contribute to the rejection transplant organs.

It was also shown that the prototype $2'-5'A_3$ exhibited no immunosuppressive activity at concentrations of 500 µg/kg. Kimchi et al, 1983 recommended a 23–700 µg/kg dose of $2'-5'A_3$ in their U.S. Pat. No. 4,378,352. Evidently, even with such high concentrations, the drug was quickly hydrolyzed in blood to inactive components.

Thus it was shown, that the resistance of $(2'-5')A_2A_{r\text{-}epoxy}$ and $(2'-5')A_2A^{l\text{-}epoxy}$ to enzymatic splitting correlates with the level of their immunosuppressive activity.

A more detailed investigation of the action of $(2'-5')A_2A_{r\text{-}epoxy}$ on the immune system of monkeys showed that this analogue suppresses production of interleukin-II and stimulates the level of α-interferon and γ-interferon in blood lymphocytes for a period of two weeks (Table 11 and 12). At the same time the quantity of α-interferon in blood plasma tends to normalize.

TABLE 11

Effect of Single Intravenous Administration of $(2'-5')A_2A_{r\text{-}epoxy}$ on the Immune System of Macaque Rh. Monkeys at a Dose of 25 µg/kg

| Type of assay* | Days following the administration of $(2'-5')A_2A_{r\text{-}epoxy}$ | | | | | |
|---|---|---|---|---|---|---|
| | 0 | 1 | 2 | 4 | 8 | 12 | 21 |
| α-interferon of plasma | 8 | 8 | 4 | — | — | 4 | 4 |
| γ-interferon of lymphocytes | 4 | 16 | 16 | — | — | 16 | 8 |
| α-interferon of lymphocytes | 16 | 32 | 32 | — | — | 32 | 16 |
| Interleukin-II | 4 | 2 | 2 | — | — | 2 | 4 |

*Units per 10,000 lymphocytes.

TABLE 12

Effect of Single Intravenous Administration of
$(2'-5')A_2A_{r-epoxy}$ on the Immune System of
Macaque Rh. Monkeys at a Dose of 50 µg/kg

| Type of assay* | Days following the administration of $(2'-5')A_2A_{r-epoxy}$ | | | | | | |
|---|---|---|---|---|---|---|---|
| | 0 | 1 | 2 | 4 | 8 | 12 | 21 |
| α-interferon of plasma | 16 | 32 | 4 | — | — | 4 | 4 |
| γ-interferon of lymphocytes | 4 | 8 | 32 | — | — | 32 | 8 |
| α-interferon of lymphocytes | 32 | 32 | 64 | — | — | 64 | 32 |
| Interleukin-II | 8 | 4 | 4 | — | — | 4 | 4 |

*Units per 10,000 lymphocytes

From Table 12, it is apparent that, in its action, $(2'-5')A_2A_{r-epoxy}$ differs from the widely used immunosuppressor cyclosporine which, while suppressing the quantity of γ-interferon, shows a negative effect on the antiviral and antimicrobial protection of the organism.

EXAMPLE 7

Kidney Allotransplantation Using Chinchilla Rabbits

Due to the fact that the best immunosuppressive activity which we have studied was exhibited by the compound $(2'-5')A_2A_{r-epoxy}$ in the animal experiments using kidney transplantation, further investigation was directed to that analogue.

Kidney allotransplantations were performed using chinchilla rabbits of the same sex, weighing 5.0–6.5 kg. In the series of 10 rabbits, allogenic kidneys were transplanted on the neck vessels, rabbit ureter was taken outside for performing ureterocutaneostoma. Anastomosis was performed on the donor kidney vessels according to the "end-into-end" pattern, with the external carotid artery and the jugular vein joined by means of their preliminary cannulation and fixation by the cannulae with the recipient vessels.

The recipient rabbits had combined anesthesia: intravenous introduction of hexenal at a rate of 10 mg per 1.0 kg. body weight was supplemented by local anesthesia with 0.25–0.5% novocaine solution up to 15.0 ml. An intact rabbit served as a kidney donor, whose kidneys were exposed by means of transperitoneal access and perfused with 500 ml of Eurocollins solution, in situ. Simultaneously with the kidney perfusion, kidney vessels and ureters were utilized, the latter being cut at the level of iliac vessels. Having performed perfusion without extracting a kidney from the donor, kidney vessels were cannulated from the aorta and vena cava, the canulae were fixed with separate ligatures and the vessels were released. After this, the kidney was extracted.

The organs were preserved at the temperature of melting ice. Then we proceeded directly to kidney transplantation. The preservation lasted for about 2.5–3.0 hours and thermal ischemia (secondary) duration was 30–40 minutes.

Immunosuppression was performed by IV injection of $(2'-5')A_2A_{r-epoxy}$ at a dose of 5 µg per 1.0 kg body weight at 0.1 ml of the physiologic solution daily until the conclusion of the experiment. During the first two weeks of the postoperative period, blood was taken for immunological analysis; BTR with PHA and Concanavalin A were tested.

The results of the experiments were evaluated clinically, by the presence or absence of urination from the ureterocutaneostoma and by the behavior of the experimental animals.

Overall, the results may be divided into four groups. The first group containing four animals with positive results where the function of the grafted kidney was observed for at least 2 months post-transplantation; the second group also containing four rabbits, showed no function in the early postoperative period probably due to vesicular thrombosis at the anastomosis level.; the third group, a single rabbit showed a dramatic loss of function between 62 and 96 hours following the operation, most probably connected with an acute rejection reaction. The fourth group, also a single rabbit, showed negative results, postoperative wound suppuration, sepsis and death within the first week after transplantation.

Analyzing the group with positive results, it was noted that in one case, by observation of the grafted kidney's stable function 1 month following the operation, the contralateral left kidney was ablated and the grafted kidney continued functioning. However, in another similar case, nephrectomy resulted in the rabbit's death within 48 hours.

At the same time there were cases noted with infectious complications: 2 rabbits had generalized viral infection of the respiratory tract which led to their death on the $17^{th}$ and $58^{th}$ day of the post-transplantation period. In one case purulent inflammation was revealed in the graft bed, which was also fatal on the 18th day following the operation.

Lymphocyte Blast-Transformation Reaction in Operated Rabbits

Immunological investigations carried out during the two weeks following the operation revealed inhibition of the lymphocyte blast-transformation reaction in operated rabbits. The data is provided in Table 13.

TABLE 13

Lymphocyte Blast-transformation During the in vivo
Administration of $(2'-5')A_2A_{r-epoxy}$
DNA synthesis by [$^3$H]-thymidine incorporated in cpm(×10$^3$)

| | Group 1 (four rabbits) | | | Group 2 (four rabbits) | | |
|---|---|---|---|---|---|---|
| Mitogen | 48 h. pre-op. | 48 h. post-op. | 2 weeks post-op. | 48 h. pre-op. | 48 h. post-op. | 2 weeks post-op. |
| Con A | 12.6 | 1.6 | 1.6 | 11.0 | 4.4 | 5.0 |
| PHA 10 | 6.0 | 0.9 | 1.5 | 7.0 | 2.4 | 2.1 |
| PHA 20 | 2.1 | 1.2 | 1.6 | 1.4 | 5.5 | — |
| Spontaneous | 0.648 | 0.306 | — | 0.597 | 0.274 | — |

The complications observed in the second group were surgical in nature (imperfect technique of vascular anastomosis). The appearance of vascular thrombosis manifested by a dramatic fall of the grafted kidney's function occurred on average on the 8th day, of the postoperative period. In all cases, the presence of blood clots in both the donor and the recipient were noted.

EXAMPLE 8

Macaque Rh. Kidney Cross—Allotransplantation

The experiments were performed on 4 year-old Macaque Rh. monkeys. Each cohort consisted of 3 animals. The animals were observed for a period of 3 consecutive months. The results of the experiments were evaluated clinically: by the presence or absence of urination from the ureterocutaneostoma.

Experimental Technique
Animals: Group 1
Orthotopic grafting of the donor kidney

After intravenous anesthesia with Ketalar®, an extraperitoneal access to the left kidney was performed through layer by layer cuts to the left lumbar region. The kidney was excised from the surrounding tissues. A clamp was applied to the vessel limb; the artery, the vein and the ureter each were prepared for anastomosis separately. The kidney was excised and transferred for hypothermal conservation in Collins' solution.

The donor kidney was transplanted into the recipient. Vesicular anastomosis was performed: the graft arteries and veins attached to the appropriate recipient kidney vessels through plastic tubes. The kidney having been resuscitated by in blood flow, acquired the normal color and turgor. Additional hemostasis in the wound was performed. Ureterocutaneostomy was performed, which was followed by applying layer-upon-layer sutures on the wound and its aseptic dressing.

Animals: Group 2
Heterotopic grafting of the donor kidney

The monkeys were narcotized by means of the intravenous anesthesia with Ketalar® and subjected to medial laparotomy from the xiphoid down to the pubic joint. Access to the left Kidney was made extraperitoneally. The kidney was teased from the surrounding tissues. A clamp was put on the vessel limb; the artery, the vein and the ureter were dressed separately; the kidney was cut and transferred for hypothermal conservation in Collins' solution.

The internal iliac artery and the external iliac vein were extracted extra-peritoneally, immobilized and prepared for anastomosis. The donor kidney was transferred to the recipient. Vessel anastomosis was performed: the graft arteries were anastomosed with the internal iliac artery according to the end-to-end method and the graft veins were anastomosed with the external iliac vein according to the end-to-side method. The kidney having been engaged in blood flow, acquired a normal color and turgor. Bleeding on the line of the arterial anastomosis was stopped by making additional sutures. Ureterocutaneostomy was performed. The abdominal cavity was lavaged with the solution of disodium carbenicillin. Layer-upon-layer sutures on the wound were applied. Aseptic dressing was performed.

TABLE 14

Effect of Intravenous Administrations of $(2'-5')A_2A_{r\text{-epoxy}}$ (50 μg/kg) on the Immune System of Macaque Rh. Monkeys After Kidney Transplantation

| Type of assay | 2 days pre-op. | Day 1 | Days post-operation |     |     |     |
|---|---|---|---|---|---|---|
|   |   |   | 5 | 8 | 13 | 18 |
| IgG (g/l) | 13 | — | 12.2 | 12.75 | — | — |
| IgA (g/l) | 0.4 | — | 2.07 | 2.5 | — | — |
| IgM (g/l) | 0.8 | — | 0.75 | 0.86 | — | — |
| T-helpers (%) | 30 | 8 | 39.9 | 32 | 34.7 | 14.5 |
| T-suppress (%) | 44 | 40.6 | 44 | 47 | 47.7 | 57.5 |
| T-killers (%) | 19 | 5 | 19 | 22 | 22.6 | 16 |

During our experiments we have divided monkeys into two groups, three monkeys to each group. For the first group $(2'-5')A_2A_{r\text{-epoxy}}$ was administered intravenously at concentration of 50 μg/kg two days before the operation and at the second, sixth, and twelfth day after the operation and then every sixth day. The data shows that $(2'-5')A_2 A_{r\text{-epoxy}}$ selectively inhibits the subpopulation of T-lymphocytes, which have been documented to be critical in the rejection of transplants. After five days the quantity of T-killers and T-helpers returned back to normal and at 18 days their numbers had been reduced two-fold (Table 14). After transplantation kidney functions were restored within 10 hours.

The administration schedule of $(2'-5')A_2 A_{r\text{-epoxy}}$ was modified slightly for the second group of monkeys. The preparation was injected two days before the operation and every other day at a concentration of 50 μg/kg during the entire post-transplantation period. It was found that the normal function of the kidney was reinstituted in the transplanted monkeys within 10 hours. Immunological analyses showed that 7 days after surgery, the quantity of T-suppressors increased from 44% (presurgical level) to 49%. The number of T-helpers dropped correspondingly from 37% to 7%. Analogous suppression effect was shown for the T-killers. During the entire postoperative period, this activity tendency continues.

The results seem to indicate that $(2'-5')A_2 A_{r\text{-epoxy}}$ in concentrations of 50 μg/kg effectively prevent the rejection of the transplanting organs, insures the normal functioning of transplanted kidney and slows the growth of the T-helper and T-killer cells in experimental animals during the postoperative period.

We claim:

1. Adenylyl (2'-5')adenylyl (2'-5')-9-( 2,3-anhydro-β-D-ribofuranosyl)adenine disodium salt.

2. Adenylyl (2'-5')adenylyl (2'-5')-9-( 2,3-anhydro-β-D-lyxofuranosyl)adenine disodium salt.

3. A pharmaceutical composition comprising adenylyl (2'-5')adenylyl(2'-5')-9-( 2,3-anhydro-β-D-ribofuranosyl)adenine disodium salt and a pharmaceutically acceptable carrier.

4. A pharmaceutical composition comprising adenylyl (2'-5')adenylyl (2'-5')-9-( 2,3-anhydro-β-D-lyxofuranosyl) adenine disodium salt and a pharmaceutically acceptable carrier.

5. A method for inhibiting the host-vs.-graft reaction comprising administering to a mammal in need of such treatment an effective amount of a compound according to claim 1.

6. A method for inhibiting the host-vs.-graft reaction comprising administering to a mammal in need of such treatment an effective amount of a compound according to claim 2.

7. A method for inhibiting the host-vs.-graft reaction comprising administering to a mammal in need of such treatment an effective amount of a pharmaceutical composition according to claim 3.

8. A method for inhibiting the host-vs.-graft reaction comprising administering to a mammal in need of such treatment an effective amount of a pharmaceutical composition according to claim 4.

* * * * *

UNITED STATES PATENT AND TRADEMARK OFFICE
CERTIFICATE OF CORRECTION

PATENT NO. : 5,571,799
DATED : November 5, 1996
INVENTOR(S) : TKACHUK et al

It is certified that error appears in the above-identified patent and that said Letters Patent is hereby corrected as shown below:

Column 2, line 26, "ppA(2'A)$_n$" should read --pppA(2'A)$_n$--.
Column 6, line 12, "(Chemapoe" should read --(Chemapol--.
Column 6, line 31, "sulfone chloroide" should read --sulfonyl chloride--.
Column 6, line 38, "40/100" should read --40/100$\mu$--.
Column 6, line 43, "R-toluene" should read --p-toluene--.
Column 6, line 49, "40/100" should read --40/100$\mu$--.
Column 6, line 58, "sulfone" should read --sulfonyl--.
Column 8, line 38, "column" should read --L column--.
Column 8, line 53, "column" should read --L column--.
Column 11, Table 5, lines 2 and 4 after "TABLE 5", "(2'-5')A$_2$A$_{r\text{-epoxy}}$" should read --(2'-5')A$_2$A$_{\ell\text{-epoxy}}$--.

Figure 2:
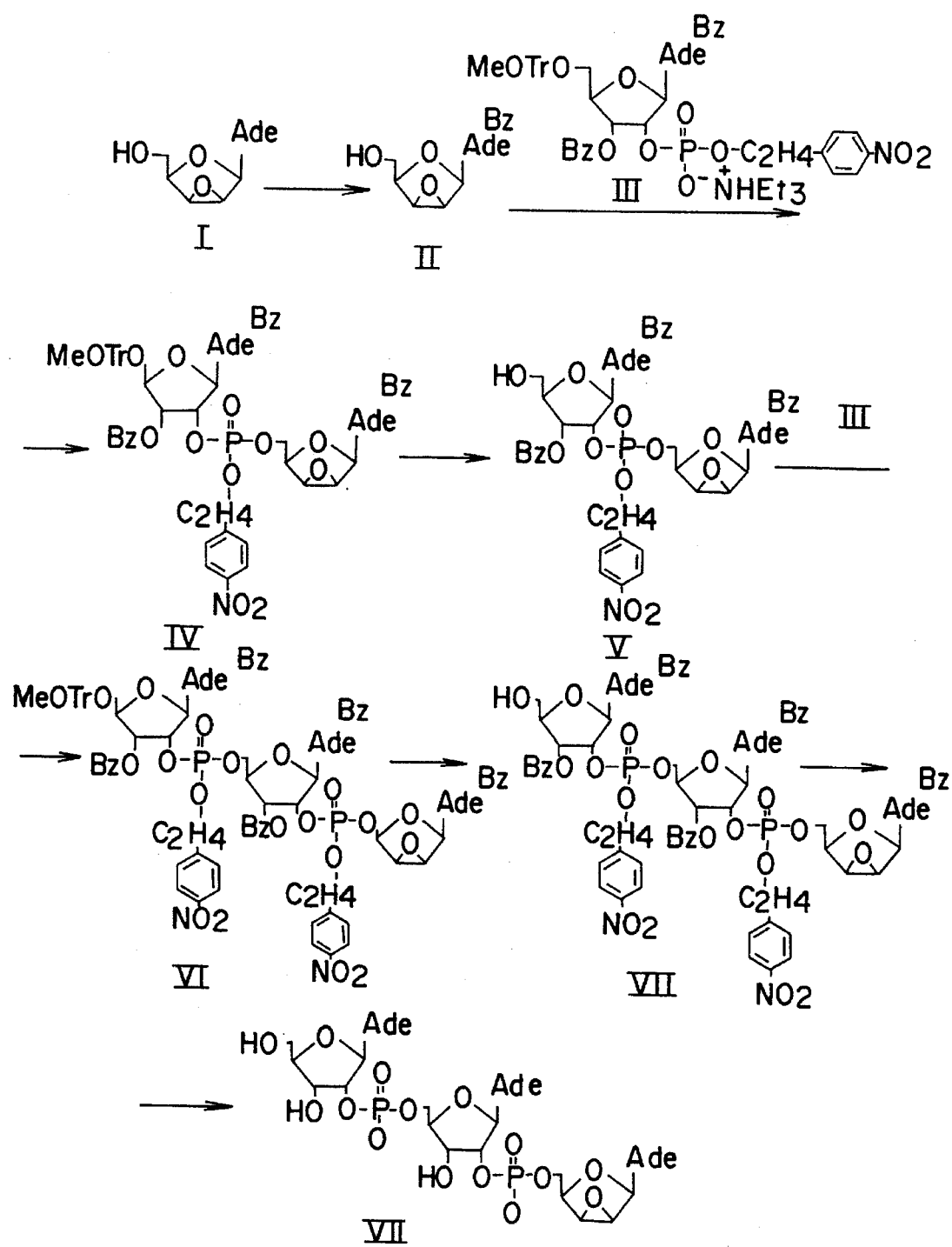
FIG. 2 is a schemtaic diagram for the synthesis of (2'-5')$A_2A^{l\text{-}epoxy}$.

Figure 1, in formulas III, IV, and VI, "UTrO" should read --MTrO--.
Figure 1, in the formula at the lower right corner "UTr" should read --MTr--.
Figure 1, in formula III, "O-NHCt$_3$" should read --O-NHEt$_3$--.
Figure 1, the entire caption at line 2 from the bottom should read --(2'-5')-9-(2,3-ANHYDRO-ß-D-RIBOFURANOSYL) ADENINE--.
Figure 2, in formulas III, IV and VI, "MeOTrO" should read --MOTrO--.
Figure 2, the entire caption at line 2 from the bottom should read --(2'-5')-9-(2,3-ANHYDRO-ß-D-LYXOFURANOSYL) ADENINE--.

Signed and Sealed this

Twenty-ninth Day of September, 1998

*Attest:*

BRUCE LEHMAN

*Attesting Officer*    Commissioner of Patents and Trademarks